(12) United States Patent
Cao et al.

(10) Patent No.: US 11,490,919 B2
(45) Date of Patent: Nov. 8, 2022

(54) MINIMALLY INVASIVE ULTRASONIC OSTEOTOME HEAD AND MINIMALLY INVASIVE ULTRASONIC BONE POWER SYSTEM

(71) Applicant: BEIJING SMTP TECHNOLOGY CO., LTD., Beijing (CN)

(72) Inventors: Qun Cao, Beijing (CN); Zhenzhou Li, Beijing (CN); Songtao Zhan, Beijing (CN)

(73) Assignee: Beijing SMTP Technology Co., Ltd., Beijing (CN)

( * ) Notice: Subject to any disclaimer, the term of this patent is extended or adjusted under 35 U.S.C. 154(b) by 566 days.

(21) Appl. No.: 16/479,555

(22) PCT Filed: Jan. 29, 2018

(86) PCT No.: PCT/CN2018/074409
§ 371 (c)(1),
(2) Date: Jul. 19, 2019

(87) PCT Pub. No.: WO2019/134206
PCT Pub. Date: Jul. 11, 2019

(65) Prior Publication Data
US 2019/0357930 A1    Nov. 28, 2019

(51) Int. Cl.
*A61B 17/32*    (2006.01)
*A61B 34/00*    (2016.01)
(Continued)

(52) U.S. Cl.
CPC .... *A61B 17/32002* (2013.01); *A61B 17/1626* (2013.01); *A61B 17/1659* (2013.01);
(Continued)

(58) Field of Classification Search
CPC ...... A61B 17/320068; A61B 17/32002; A61B 17/320016
See application file for complete search history.

(56) References Cited

U.S. PATENT DOCUMENTS

| 5,346,469 A | 9/1994 | Ikeda et al. |
| 2006/0004396 A1 | 1/2006 | Easley et al. |

(Continued)

FOREIGN PATENT DOCUMENTS

| CN | 102843979 A | 12/2012 |
| CN | 103431894   | 12/2013 |

(Continued)

OTHER PUBLICATIONS

PCT/CN2018/074409, "International Preliminary Report on Patentability", dated Aug. 4, 2020, 5 pages.

(Continued)

*Primary Examiner* — Andrew Yang
(74) *Attorney, Agent, or Firm* — Kilpatrick Townsend & Stockton LLP

(57) ABSTRACT

A minimally invasive ultrasonic osteotome head and a minimally invasive ultrasonic powered system for bone; the minimally invasive ultrasonic osteotome head comprises an osteotome rod (11, 21, 31, 41, 51, 61) and a head end (12, 22, 32, 42, 52, 62), the head end (12, 22, 32, 42, 52, 62) being located at a front end of the osteotome rod(11, 21, 31, 41, 51, 61), and the head end (12, 22, 32, 42, 52, 62) being bent laterally at a certain angle, wherein knurled teeth or skewed teeth are provided on the bent portion. By means of bending the head end (12, 22, 32, 42, 52, 62), bone tissue around the transforaminal endoscope may be removed. Therefore, a surgeon may, as much as possible, have more operation space under the limited endoscope channel, thereby increasing bone removal efficiency.

15 Claims, 5 Drawing Sheets

(51) Int. Cl.
*A61B 17/16* (2006.01)
*A61B 17/00* (2006.01)

(52) U.S. Cl.
CPC ...... *A61B 17/320068* (2013.01); *A61B 34/25* (2016.02); *A61B 2017/0034* (2013.01); *A61B 2017/00119* (2013.01); *A61B 2017/00473* (2013.01); *A61B 2017/320064* (2013.01); *A61B 2017/320084* (2013.01)

(56) References Cited

U.S. PATENT DOCUMENTS

| | | | |
|---|---|---|---|
| 2006/0253050 | A1* | 11/2006 | Yoshimine ......... A61H 23/0245 601/2 |
| 2009/0326535 | A1* | 12/2009 | Blus .................... A61B 17/142 606/86 R |
| 2013/0204285 | A1 | 8/2013 | Gouery et al. |
| 2013/0267975 | A1 | 10/2013 | Timm et al. |
| 2016/0022283 | A1 | 1/2016 | Wallace et al. |
| 2017/0000513 | A1* | 1/2017 | Conlon ........ A61B 17/320068 |
| 2017/0007852 | A1* | 1/2017 | Isola .............. A61B 17/320068 |
| 2017/0172607 | A1 | 6/2017 | Houser |
| 2017/0202592 | A1 | 7/2017 | Shelton, IV et al. |

FOREIGN PATENT DOCUMENTS

| | | |
|---|---|---|
| CN | 105286775 | 2/2016 |
| EP | 2119403 | 11/2009 |
| EP | 3025659 | 6/2016 |
| EP | 3025660 | 6/2016 |
| JP | 425707 | 2/1992 |
| JP | 2006263031 | 10/2006 |
| JP | 2013519437 A | 5/2013 |
| JP | 2015536760 A | 12/2015 |
| JP | 3205419 | 7/2016 |
| JP | 3207943 | 12/2016 |
| KR | 20160000984 | 3/2016 |
| KR | 200484760 | 10/2017 |
| WO | 2006016476 | 2/2006 |
| WO | 2014088899 | 6/2014 |
| WO | 2017171034 | 10/2017 |
| WO | 2018001050 | 1/2018 |
| WO | 2018006705 | 1/2018 |

OTHER PUBLICATIONS

International Application No. PCT/CN2018/074409, International Search Report dated Aug. 31, 2018, 2 pages.

* cited by examiner

MINIMALLY INVASIVE ULTRASONIC OSTEOTOME HEAD AND MINIMALLY INVASIVE ULTRASONIC BONE POWER SYSTEM

TECHNICAL FIELD

The present disclosure relates to the technical field of medical instruments and, in particular, to a minimally invasive ultrasonic osteotome head and a minimally invasive ultrasonic bone power system.

BACKGROUND

With the development of modern medical technology, minimally invasive surgery under a transforaminal endoscope has been widely applied to the clinical orthopedic surgery. The existing power tool under a transforaminal endoscope is mainly a high-speed grinding drill that removes bone tissues by high-speed rotation of a grinding drill head. Due to the rotating operation mode, the grinding drill is easy to scrape soft tissue during an operation to cause a wire drawing effect, and is easy to cause a blind view due to blood such that a medical person will have an unclear vision, which might further cause medical accidents.

An ultrasonic bone power system is a power tool using ultrasonic energy to perform an operation, and has outstanding characteristics such as precise cutting/aspiration, no damage to soft tissues including blood vessels and nerves, and low temperature for hemostasis. The minimally invasive ultrasonic bone power system combines both the minimally invasive feature and ultrasonic feature, and realizes the ultrasonic cutting operation for bone tissues by means of a tool channel of a transforaminal endoscope, thereby greatly enriching approaches in spinal surgery and improving the safety of spinal surgery. However, the transforaminal endoscope has a tool hole with a small diameter, with the diameter of an operation channel being usually 2-6 mm, while the entire channel has a longer length, usually above 20 cm. When an ultrasonic osteotome head system is inserted into the transforaminal endoscope, due to the limitation of the ultrasound, the osteotome head cannot be bent laterally in the transforaminal endoscope. Therefore, the operating space is very limited, and the operation could be carried out only in a direction of the transforaminal endoscope, such that the bone tissues around the transforaminal endoscope cannot be removed, thus impossible to achieve the maximum efficiency of the ultrasonic osteotome.

SUMMARY OF THE INVENTION

The present disclosure provides a minimally invasive ultrasonic osteotome head and a minimally invasive ultrasonic bone power system, so as to solve the problem in the prior art that the operating space is limited and bone tissues around the transforaminal endoscope cannot be removed.

In a first aspect, the present disclosure provides a minimally invasive ultrasonic osteotome head, comprising an osteotome rod and a head end, the head end being located at a front end of the osteotome rod, being characterized in that the head end bends laterally at a certain angle.

Further, the bending portion is provided with knurled teeth or skewed teeth.

Further, a bottom surface of the bending portion is a square circular arc surface, and upper and lower inclined surfaces of a transverse surface of the bending portion are provided with knurled teeth.

Further, the head end is rake-shaped, and a transverse surface of the bending portion is provided with skewed teeth.

Further, the head end is spoon-shaped, and a top surface of the bending portion is provided with knurled teeth.

Further, a transverse surface and a side surface of the bending portion are provided with skewed teeth.

Further, the head end is sheet-shaped, and a transverse surface of the bending portion is provided with skewed teeth.

Further, the head end is in a shape of a beveled square file, and a transverse surface of the bending portion is provided with knurled teeth.

Further, the head end is a prismatic cylinder, a transverse surface of the bending portion is provided with knurled teeth, and a side surface thereof is provided with a spiral skewed slot.

Further, the osteotome rod of the minimally invasive ultrasonic osteotome head comprises two detachable portions, that is a front portion connected with the head end and a rear portion connected with an ultrasonic handle.

Further, the entire osteotome rod is of a hollow structure.

Further, only part of the osteotome rod is of a hollow structure, and water is discharged through side holes in the middle of the osteotome rod.

In a second aspect, the present disclosure further provides a minimally invasive ultrasonic bone power system comprising the minimally invasive ultrasonic osteotome head.

Further, the minimally invasive ultrasonic bone power system further comprises a transforaminal endoscope, the osteotome rod of the minimally invasive ultrasonic osteotome head being fitted in a channel of the transforaminal endoscope.

The minimally invasive ultrasonic bone power system further comprises a main unit, an ultrasonic handle and a foot switch, the minimally invasive ultrasonic osteotome head being connected to the ultrasonic handle via a connecting device, and the ultrasonic handle and the foot switch being respectively electrically connected with the main unit.

Further, the main unit comprises an osteotome head detection module, a human-machine interaction module, an ultrasonic signal generator, a high voltage driver, a frequency tracking and failure detection module, and voltage, current and phase samplers.

The present disclosure replaces a high-speed grinding drill with an ultrasonic bone power system, thus reducing the medical risk, providing more precise cutting, having no damage to soft tissues such as blood vessels and nerves, and providing better hemostasis.

In the present disclosure, the head end of the minimally invasive ultrasonic osteotome head bends laterally at an angle, and bending the head end can remove bone tissues around the transforaminal endoscope, so that the operator has as much operating space as possible under a limited channel of the transforaminal endoscope, thereby improving the bone removal efficiency. Further, providing knurled or skewed teeth in the bending portion provides better grinding or cutting for the bone tissues around the transforaminal endoscope.

By configuring the osteotome rod of the minimally invasive ultrasonic osteotome head as two detachable portions, the present disclosure also solves the problem that the bending osteotome head cannot pass through the channel of the transforaminal endoscope and thus the osteotome rod cannot be fitted into the endoscope channel, thereby further facilitating assembly of the osteotome head.

DETAILED DESCRIPTION OF EMBODIMENTS

In the following embodiments, detailed description by text together with the drawings illustrate how the disclosed embodiments are implemented. It is to be understood that other embodiments are feasible, and the embodiments may be modified structurally or logically without deviating from the scope disclosed in the present disclosure.

The present disclosure will be further described in detail below with reference to specific embodiments as well as the drawings.

Embodiment 1

Figure 1:
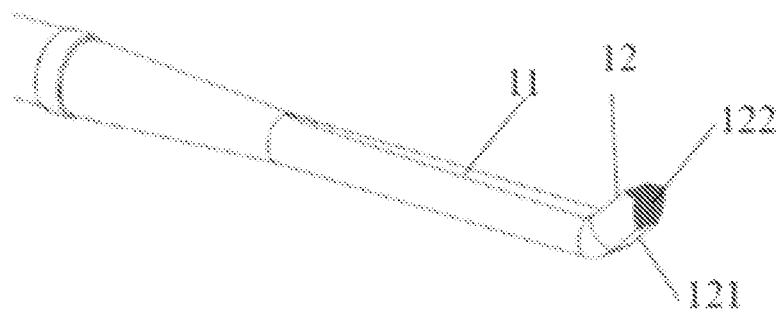
FIG. 1 is a structural schematic diagram of a minimally invasive ultrasonic osteotome head of Embodiment 1 of the present disclosure.

As shown in FIG. 1, the embodiment discloses a minimally invasive ultrasonic osteotome head 1, which comprises an osteotome rod 11 and a head end 12, the head end 12 being located at a front end of the osteotome rod 11 and bending laterally at a certain angle. A bottom surface 121 of the bending portion is a square arc surface, and upper and lower inclined surfaces of a transverse surface 122 of the bending portion are provided with knurled teeth.

Figure 2:
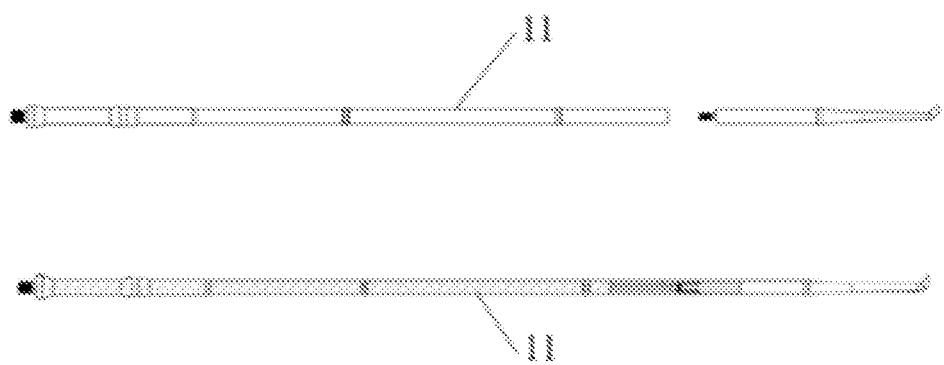
FIG. 2 is a structural schematic diagram of an osteotome rod of a minimally invasive ultrasonic osteotome head of Embodiment 1 of the present disclosure.

In the assembly procedure, since the bending head end cannot pass through the channel of the transforaminal endoscope, in order to enable the minimally invasive ultrasonic osteotome head 1 to operate together with the transforaminal endoscope, as shown in FIG. 2, the osteotome rod 11 of the minimally invasive ultrasonic osteotome head is configured as two portions, a front portion connected with the head end 12 and a rear portion connected with an ultrasonic handle. The two portions are connected by means of threads by which the front portion of the osteotome head can be tightly connected with the rear portion to form the complete osteotome rod 11. During installation, the rear portion connected to the handle is inserted from the rear of the endoscope, and the front portion of the osteotome rod connected to the bending head end is inserted from the front of the endoscope, and the two portions are tightly connected by means of threads. The connection position where the two portions are connected may be in the middle of the osteotome rod 11, at a rear end of the osteotome rod 11, or on a side of the osteotome rod near the head end 12.

The osteotome rod 11 may be of a hollow structure through the entire rod to discharge water for perfusion directly at the head end; or only part of the osteotome rod is of a hollow structure, so that water is discharged through side holes in the middle of the osteotome rod 11.

Figure 3:
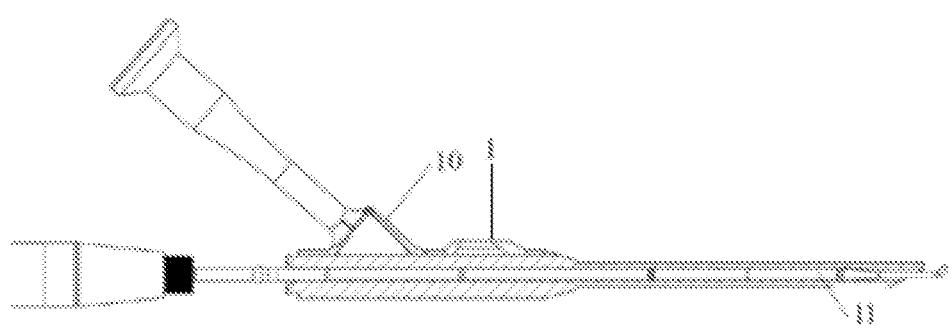
FIGS. 3 and 4 are structural schematic diagrams of a minimally invasive ultrasonic osteotome head for use, together with a transforaminal endoscope, in a minimally invasive ultrasonic bone power system of Embodiment 1 of the present disclosure.
Figure 4:
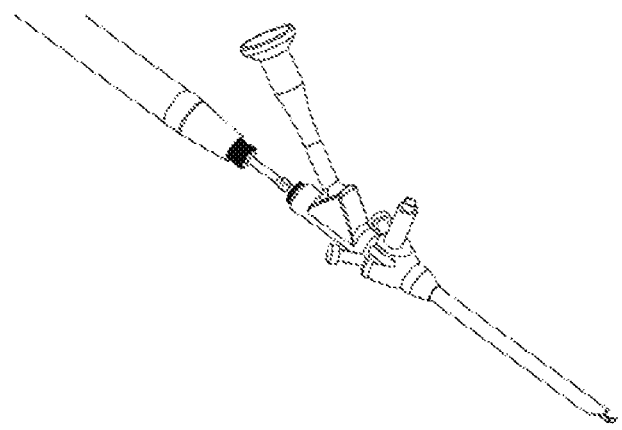

The minimally invasive ultrasonic osteotome head 1 can be used, together with a transforaminal endoscope, in a minimally invasive ultrasonic bone power system. As shown in FIGS. 3-4, when in use, the osteotome rod of the minimally invasive ultrasonic osteotome 1 is fitted in an operation channel of the transforaminal endoscope 10 and is connected to the ultrasonic handle via a connecting device. The ultrasonic handle is electrically connected with a main unit, and a foot switch is further provided and also electrically connected with the main unit. The main unit, the connecting device, the ultrasonic handle, the foot switch, the minimally invasive ultrasonic osteotome head and other components constitute an ultrasonic bone power system. In the above components, the foot switch is used to control the main unit to start or stop and further control the output and stop of ultrasound; the main unit is used to detect the access of the ultrasonic handle, control and adjust ultrasonic driving signals so that the ultrasonic system can operate at the optimal resonance frequency, and also identify and detect the vibration state of the handle, such as identifying current, voltage and phase parameters of the ultrasonic driving signal, and detecting whether the driving signal is over-current, open-circuit or short-circuit; the ultrasonic handle is used to convert a high voltage electrical signal into ultrasound vibration to drive the ultrasonic osteotome head to operate; and the minimally invasive ultrasonic osteotome head 1 is used to transfer and amplify the ultrasonic vibration to realize the bone tissue resection. Meanwhile, since the head end 12 of the minimally invasive ultrasonic osteotome head 1 bends laterally, the bone tissues around the transforaminal endoscope can be removed, so that the operator has as much operating space as possible even under a limited channel of the endoscope, thereby improving the bone removal efficiency. In addition, the upper and lower inclined surfaces of the transverse surface 122 of the bending portion are provided with knurled teeth, which is more advantageous for grinding the bone tissues around the endoscope, thereby further improving the efficiency.

Figure 5:
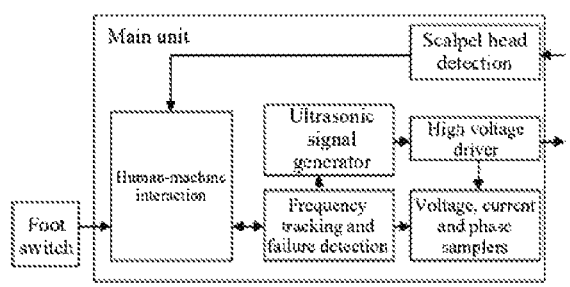
FIG. 5 is a composition structural schematic diagram of a main unit of a minimally invasive ultrasonic bone power system of Embodiment 1 of the present disclosure.

As shown in FIG. 5, the main unit of the minimally invasive ultrasonic bone power system comprises an osteotome head detection module, a human-machine interaction module, an ultrasonic signal generator, a high voltage driver, a frequency tracking and failure detection module, and voltage, current and phase samplers. The osteotome head detection module is used to identify whether an ultrasonic handle is connected to the main unit so as to prevent the main unit from outputting a high voltage driving signal without the ultrasonic handle. The human-machine interaction module identifies, via circuits, the operation of the foot switch, the detection of the osteotome head, control inputs of user power and operation mode, display of abnormal states of the circuits, etc., and controls the operation of the frequency tracking and failure detection module and other components, sending a control signal to the ultrasonic signal generator to make it start or stop producing a ultrasonic frequency signal as set. The ultrasonic signal generated by the ultrasonic signal generator is output to the high voltage driver, which drives the ultrasonic handle. The voltage, current and phase samplers sample the voltage and current in the driving circuit of the ultrasonic handle and the phase relationship thereof. The frequency tracking and failure detection module adjusts the frequency and the phase of the ultrasonic signal generator according to the acquired voltage, current and phase so as to make the ultrasonic handle operate in the optimal working state, and can also be used to identify abnormal working states, including short circuit and open circuit, of the ultrasonic handle, and feed the results back to the human-machine interaction module for user query.

Embodiment 2

Figure 6:
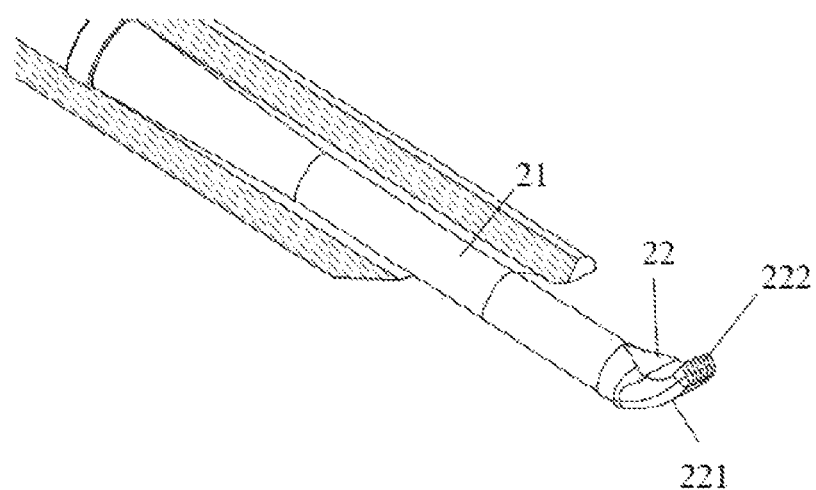
FIG. 6 is a structural schematic diagram of a minimally invasive ultrasonic osteotome head of Embodiment 2 of the present disclosure.

FIG. 6 shows a minimally invasive ultrasonic osteotome head 2 of Embodiment 2 of the present disclosure. The osteotome head 2 comprises an osteotome rod 21 and a head end 22, the head end 22 being located at a front end of the osteotome rod 21 and bending laterally at a certain angle. The head end 22 is of a rake-shape, and a transverse surface 222 of the bending portion is provided with skewed teeth.

Similar to Embodiment 1, in order to facilitate assembly, the osteotome rod 21 is also configured as two portions, a front portion connected to the head end 22 and a rear portion connected to the handle, the two portions being connected by means of threads. The osteotome rod 21 may be of a hollow structure through the entire rod to discharge water for perfusion directly at the head end; or only part of the osteotome rod is of a hollow structure, so that water is discharged through side holes in the middle of the rod.

The minimally invasive ultrasonic osteotome head 2 may also be used, together with a transforaminal endoscope, in a minimally invasive ultrasonic bone power system. When in use, the osteotome rod of the minimally invasive ultrasonic osteotome 2 is fitted in an operation channel of the transforaminal endoscope and is connected to the ultrasonic handle via a connecting device. The ultrasonic handle is electrically connected with a main unit, and a foot switch is further provided and also electrically connected with the main unit. Since the head end 22 of the minimally invasive ultrasonic osteotome head 2 has a laterally bending arc section, the bone tissues around the transforaminal endoscope can be removed, so that the operator has as much operating space as possible even under a limited channel of the endoscope, thereby improving the bone removal efficiency. In addition, the transverse surface 222 of the bending portion is provided with skewed teeth, which help to cut the bone tissues around the transforaminal endoscope, thereby further improving the efficiency.

Embodiment 3

Figure 7:
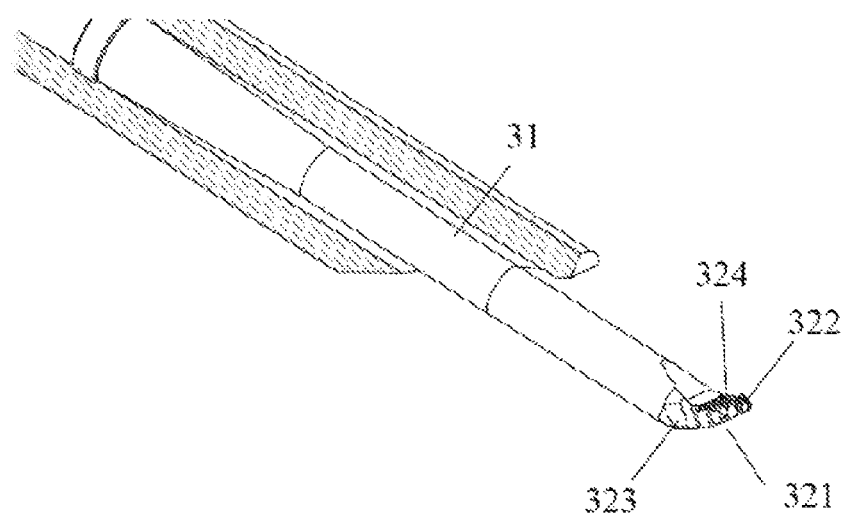
FIG. 7 is a structural schematic diagram of a minimally invasive ultrasonic osteotome head of Embodiment 3 of the present disclosure.

FIG. 7 is a minimally invasive ultrasonic osteotome head 3 of Embodiment 3 of the present disclosure. The osteotome head 3 comprises an osteotome rod 31 and a head end 32, the head end 32 being located at a front end of the osteotome rod 31 and bending laterally at a certain angle. The head end 32 is spoon-shaped, and a top surface 324 of the bending portion is provided with knurled teeth. Further, a transverse surface 322 and a side surface 323 of the bending portion could be provided with skewed teeth.

Similar to Embodiment 1, in order to facilitate assembly, the osteotome rod 31 is also configured as two portions, a front portion connected to the head end 32 and a rear portion connected to the handle, the two portions being connected by means of threads. The osteotome rod 31 may be of a hollow structure through the entire rod to discharge water for perfusion directly at the head end; or only part of the osteotome rod is of a hollow structure, so that water is discharged through side holes in the middle of the osteotome rod.

The minimally invasive ultrasonic osteotome head 3 can be used, together with a transforaminal endoscope, in an ultrasonic bone tissue surgical system. When in use, the osteotome rod 31 of the minimally invasive ultrasonic osteotome 3 is fitted in an operation channel of the transforaminal endoscope and is connected to the ultrasonic handle via a connecting device. The ultrasonic handle is electrically connected with a main unit, and a foot switch is further provided and also electrically connected with the main unit. Since the head end 32 of the minimally invasive ultrasonic osteotome head 3 bends laterally and has a trapezoidal bottom surface, the bone tissues around the transforaminal endoscope can be removed, so that the operator has as much operating space as possible even under a limited channel of the endoscope, thereby improving the bone removal efficiency. In addition, the top surface 324 of the bending portion is provided with knurled teeth, which help to grind the bone tissues around the endoscope. Further, the transverse surface 322 and the side surface 323 of the bending portion are provided with skewed teeth, which help to cut the bone tissues around the endoscope. The above configuration can improve the bone removal efficiency to a greater extent, thereby providing a larger operating space.

Embodiment 4

Figure 8:
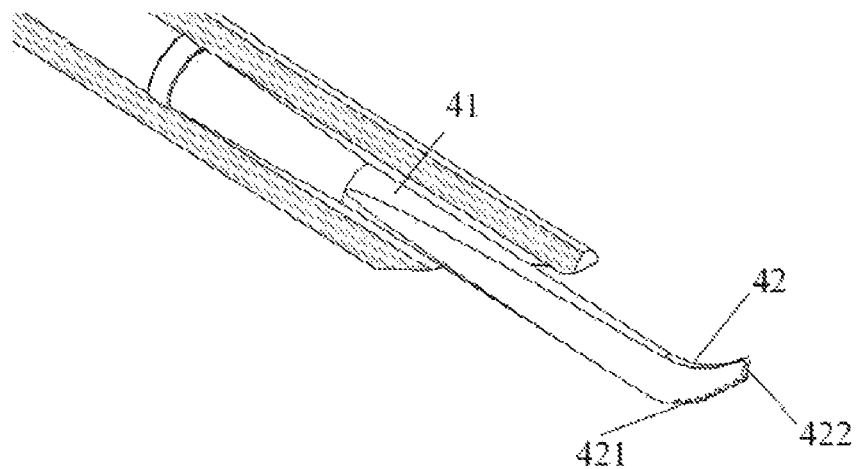
FIG. 8 is a structural schematic diagram of a minimally invasive ultrasonic osteotome head of Embodiment 4 of the present disclosure.

FIG. 8 is a minimally invasive ultrasonic osteotome head 4 of Embodiment 4 of the present disclosure. The osteotome head 4 comprises an osteotome rod 41 and a head end 42, the head end 42 being located at a front end of the osteotome rod 41 and bending laterally at a certain angle. The head end 42 is sheet-shaped, and a transverse surface 422 and a bottom surface 421 of the bending portion are provided with skewed teeth.

Similar to Embodiment 1, in order to facilitate assembly, the osteotome rod 41 is also configured as two portions, a front portion connected to the head end 42 and a rear portion connected to the handle, the two portions being connected by means of threads. The osteotome rod 41 may be of a hollow structure through the entire rod to discharge water for perfusion directly at the head end; or only part of the osteotome rod is of a hollow structure, so that water is discharged through side holes in the middle of the osteotome rod.

The minimally invasive ultrasonic osteotome head 4 can be used, together with a transforaminal endoscope, in an ultrasonic bone tissue surgical system. When in use, the osteotome rod 41 of the minimally invasive ultrasonic osteotome 4 is fitted in an operation channel of the transforaminal endoscope and is connected to the ultrasonic handle via a connecting device. The ultrasonic handle is electrically connected with a main unit, and a foot switch is further provided and also electrically connected with the main unit. Since the head end 42 of the minimally invasive ultrasonic osteotome head 4 bends laterally, the bone tissues around the transforaminal endoscope can be removed, so that the operator has as much operating space as possible even under a limited channel of the endoscope, thereby improving the bone removal efficiency. In addition, a bottom surface 421 and a transverse surface 422 of the bending portion are provided with skewed teeth, which help to cut the bone tissues around the transforaminal endoscope, thereby further improving the bone removal efficiency.

Embodiment 5

Figure 9:
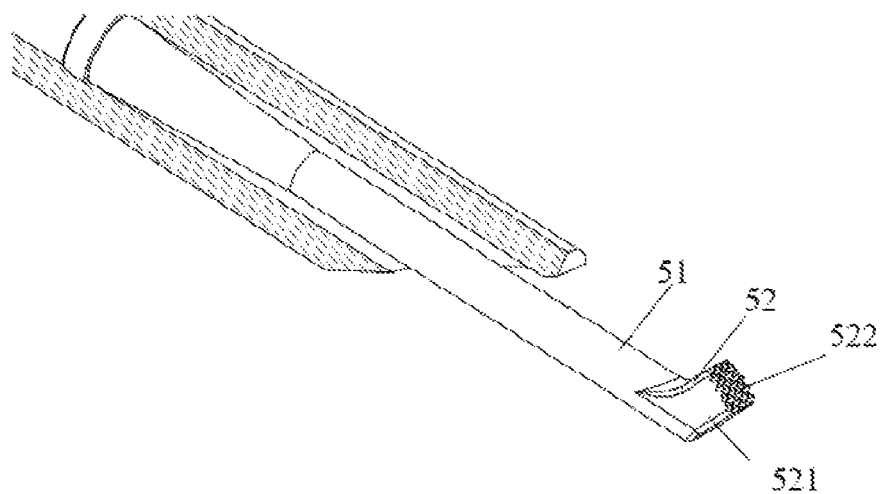
FIG. 9 is a structural schematic diagram of a minimally invasive ultrasonic osteotome head of Embodiment 5 of the present disclosure.

FIG. 9 is a minimally invasive ultrasonic osteotome head 5 of Embodiment 5 of the present disclosure. The osteotome head 5 comprises an osteotome rod 51 and a head end 52, the head end 52 being located at a front end of the osteotome rod 51 and bending laterally at a certain angle. The head end 52 is in a shape of a beveled square file, and a transverse surface 522 of the bending portion is provided with knurled teeth.

Similar to Embodiment 1, in order to facilitate assembly, the osteotome rod 51 is also configured as two portions, a front portion connected to the head end 52 and a rear portion connected to the handle, the two portions being connected by means of threads. The osteotome rod 51 may be of a hollow structure through the entire rod to discharge water for perfusion directly at the head end; or only part of the osteotome rod is of a hollow structure, so that water is discharged through side holes in the middle of the osteotome rod.

The minimally invasive ultrasonic osteotome head 5 can be used, together with a transforaminal endoscope, in an ultrasonic bone tissue surgical system. When in use, the osteotome rod 51 of the minimally invasive ultrasonic osteotome 5 is fitted in an operation channel of the transforaminal endoscope and is connected to the ultrasonic handle via a connecting device. The ultrasonic handle is electrically connected with a main unit, and a foot switch is further provided and also electrically connected with the main unit. Since the head end 52 of the minimally invasive ultrasonic osteotome head 5 bends laterally, the bone tissues around the transforaminal endoscope can be removed, so that the operator has as much operating space as possible even under a limited channel of the endoscope, thereby improving the bone removal efficiency. In addition, the transverse surface 522 of the bending portion is provided with knurled teeth, which help to grind the bone tissues around the endoscope, thereby further improving the bone removal efficiency.

Embodiment 6

Figure 10:
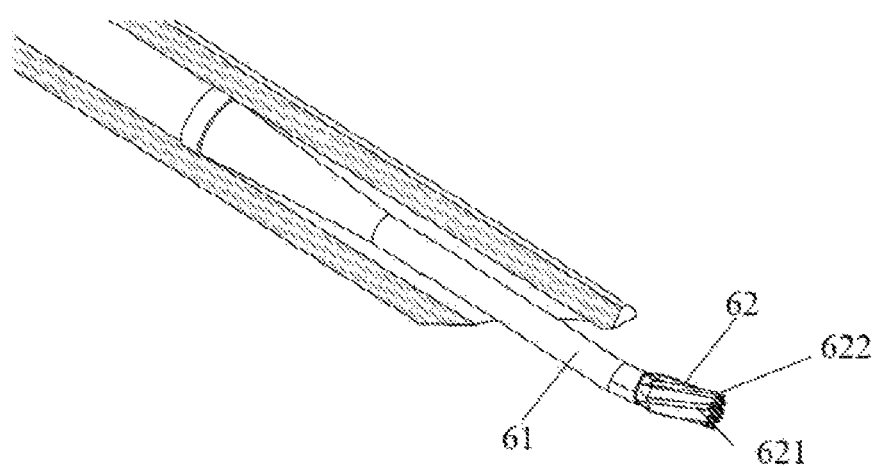
FIG. 10 is a structural schematic diagram of a minimally invasive ultrasonic osteotome head of Embodiment 6 of the present disclosure.

FIG. 10 is a minimally invasive ultrasonic osteotome head 6 of Embodiment 6 of the present disclosure. The osteotome head 6 comprises an osteotome rod 61 and a head end 62, the head end 62 being located at a front end of the osteotome rod 61 and bending laterally at a certain angle. The head end 62 is a prismatic cylinder. A transverse surface 622 of the bending portion is provided with knurled teeth, and a side surface 621 thereof is provided with a spiral skewed groove.

Similar to Embodiment 1, in order to facilitate fitting, the osteotome rod 61 is also configured as two portions, a front portion connected to the head end 62 and a rear portion connected to the handle, the two portions being connected by means of threads. The osteotome rod 61 may be of a hollow structure through the entire rod to discharge water for perfusion directly at the head end; or only part of the osteotome rod is of a hollow structure, so that water is discharged through side holes in the middle of the osteotome rod.

The minimally invasive ultrasonic osteotome head 6 can be used, together with a transforaminal endoscope, in an ultrasonic bone tissue surgical system. When in use, the osteotome rod 61 of the minimally invasive ultrasonic osteotome 6 is fitted in an operation channel of the transforaminal endoscope and is connected to the ultrasonic handle via a connecting device. The ultrasonic handle is electrically connected with a main unit, and a foot switch is further provided and also electrically connected with the main unit. Since the head end 62 of the minimally invasive ultrasonic osteotome head 6 bends laterally, the bone tissues around the transforaminal endoscope can be removed, so that the operator has as much operating space as possible even under a limited channel of the endoscope, thereby improving the bone removal efficiency. In addition, the transverse surface 622 of the bending portion is provided with knurled teeth, which help to grind the bones tissue around the endoscope, thereby further improving the bone removal efficiency.

Although various embodiments have been described in detail above, those skilled in the art will appreciate that various alternative and/or equivalent embodiments may be used to substitute for the specific disclosure of the embodiments mentioned above without departing from the present disclosure. This application is intended to cover any modification and variations of the various embodiments discussed herein.

The invention claimed is:

1. A minimally invasive ultrasonic osteotome head comprising an osteotome rod (11, 21, 31, 41, 51, 61) and a head end (12, 22, 32, 42, 52, 62), the head end being located at a front end of the osteotome rod, and bending laterally at a certain angle at a bending portion thereof, being characterized in that the osteotome head is configured to be used together with a transforaminal endoscope (10) having a channel through which the head end (12, 22, 32, 42, 52, 62) cannot pass, wherein the osteotome rod (11, 21, 31, 41, 51, 61) comprises two detachable portions, a front portion connected with the head end and a rear portion connected with an ultrasonic handle so that the front portion of the osteotome rod is fitted into the channel from the front of the transforaminal endoscope and the rear portion of the osteotome rod is fitted into the channel from the rear of the transforaminal endoscope.

2. The minimally invasive ultrasonic osteotome head of claim 1, being characterized in that the bending portion is provided with knurled teeth or skewed teeth.

3. The minimally invasive ultrasonic osteotome head of claim 1, being characterized in that a bottom surface (121) of the bending portion is a square arc surface, and upper and lower inclined surfaces of a transverse surface (122) of the bending portion are provided with knurled teeth.

4. The minimally invasive ultrasonic osteotome head of claim 1, being characterized in that the head end (22) is rake-shaped, and a transverse surface (222) of the bending portion is provided with skewed teeth.

5. The minimally invasive ultrasonic osteotome head of claim 1, being characterized in that the head end (22) is spoon-shaped, and a top surface (324) of the bending portion is provided with knurled teeth.

6. The minimally invasive ultrasonic osteotome head of claim 5, being characterized in that a transverse surface (322) and a side surface (323) of the bending portion are provided with skewed teeth.

7. The minimally invasive ultrasonic osteotome head of claim 1, being characterized in that the head end (42) is sheet-shaped, and a transverse surface (422) of the bending portion is provided with skewed teeth.

8. The minimally invasive ultrasonic osteotome head of claim 1, being characterized in that the head end (42) is in a shape of a beveled square file, and a transverse surface (522) of the bending portion is provided with knurled teeth.

9. The minimally invasive ultrasonic osteotome head of claim 1, being characterized in that the head end (62) is a prismatic cylinder, a transverse surface (622) of the bending portion is provided with knurled teeth, and a side surface (621) of the bending portion is provided with a spiral skewed slot.

10. The minimally invasive ultrasonic osteotome head of claim 1, being characterized in that the entire osteotome rod is of a hollow structure.

11. The minimally invasive ultrasonic osteotome head of claim 1, being characterized in that only part of the osteotome rod is of a hollow structure, and water is discharged through side holes in the middle of the osteotome rod.

12. A minimally invasive ultrasonic bone power system comprising the minimally invasive ultrasonic osteotome head of claim 1.

13. The minimally invasive ultrasonic bone power system of claim 12, further comprising a transforaminal endoscope, the osteotome rod of the minimally invasive ultrasonic osteotome head being fitted in a channel of the transforaminal endoscope.

14. The minimally invasive ultrasonic bone power system of claim 12, further comprising a main unit, an ultrasonic handle and a foot switch, the minimally invasive ultrasonic osteotome head being connected to the ultrasonic handle via a connecting device, and the ultrasonic handle and the foot switch being respectively electrically connected with the main unit.

15. The minimally invasive ultrasonic bone power system of claim 14, being characterized in that the main unit comprises an osteotome head detection module, a human-machine interaction module, an ultrasonic signal generator, a high voltage driver, a frequency tracking and failure detection module, and voltage, current and phase samplers.

\* \* \* \* \*